United States Patent
Imai et al.

(10) Patent No.: US 6,585,514 B2
(45) Date of Patent: Jul. 1, 2003

(54) SOLUBILIZING AGENT OF CARBONATED CALCIUM HYDROXIDE-BASED ROOT CANAL FILLER AND SOLUBILIZING METHOD

(75) Inventors: Yohji Imai, Chiba (JP); Masao Abiru, Itabashi-ku (JP); Kimihiko Sato, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 10/075,463

(22) Filed: Feb. 15, 2002

(65) Prior Publication Data

US 2002/0164558 A1 Nov. 7, 2002

(30) Foreign Application Priority Data

Mar. 5, 2001 (JP) ........................................ 2001-060281

(51) Int. Cl.$^7$ ................................................. A61C 5/02
(52) U.S. Cl. ..................................... 433/224; 433/228.1
(58) Field of Search ............................... 433/224, 215, 433/228.1, 226; 424/49

(56) References Cited

U.S. PATENT DOCUMENTS

| | | | |
|---|---|---|---|
| 3,897,548 A | * 7/1975 | Katz | 424/54 |
| 5,073,363 A | 12/1991 | Pellico | 424/49 |
| 5,229,103 A | 7/1993 | Eagle et al. | 424/49 |
| 5,427,768 A | * 6/1995 | Tung | 424/52 |
| 5,460,802 A | 10/1995 | Asami et al. | 424/49 |
| 5,846,570 A | 12/1998 | Barrow et al. | 424/616 |

FOREIGN PATENT DOCUMENTS

| | | |
|---|---|---|
| EP | 0 251 542 | 1/1988 |
| WO | WO 94/09752 | 5/1994 |
| WO | WO 96/26707 | 9/1996 |

OTHER PUBLICATIONS

Derwent Abstract (Patent Abstracts of Japan), AN 1998–328363 [29], JP 10–120539, May 12, 1998.
Derwent Abstract (Patent Abstracts of Japan), AN 1995–212855 [28], JP 7–126131, May 16, 1995.
Derwent Abstract (Patent Abstracts of Japan), AN 1996–318830 [32], JP 8–143436, Jun. 4, 1996.

* cited by examiner

Primary Examiner—Kevin Shaver
Assistant Examiner—Melba Bumgarner
(74) Attorney, Agent, or Firm—Oblon, Spivak, McClelland, Maier & Neustadt, R.C.

(57) ABSTRACT

To dissolve a calcium hydroxide-based root canal filler having been carbonated and fixed within a root canal, which cannot be removed from the root canal by means of a reamer and a file, during doing the root canal treatment again, and to sterilize the root canal, the solubilizing agent of the carbonated calcium hydroxide-based root canal filler includes water containing 1 to 60% by weight of the whole of at least one acid selected from the group consisting of phosphoric acid, gluconic acid, fumaric acid, lactic acid, glycolic acid, propionic acid, malic acid, maleic acid, citric acid, succinic acid, tartaric acid, acetic acid, glycerophosphoric acid, and malonic acid; and 0.1 to 30% by weight of the whole of at least one sterilizing properties-imparting agent selected from the group consisting of an iodine preparation, a surfactant, a bactericide, hydrogen peroxide, and limonene.

2 Claims, No Drawings

SOLUBILIZING AGENT OF CARBONATED CALCIUM HYDROXIDE-BASED ROOT CANAL FILLER AND SOLUBILIZING METHOD

BACKGROUND OF THE INVENTION

1. Field of the Invention

The present invention relates to a solubilizing agent of a carbonated calcium hydroxide-based root canal filler, which is used for removal of a calcium hydroxide-based root canal filler having been carbonated and fixed to a root canal, from the root canal.

2. Description of the Conventional Art

In the dental remedy, as the remedy of pulp disease or apical periodontitis of teeth, a treatment for removing a sphacelus within a root canal or dentins on a stained root canal wall and a treatment for adjusting a root canal into a form wherein the root canal filling can be readily achieved, using an instrument such as a reamer and a file, are carried out simultaneously; and thereafter, a materially stable substance such as gutta-percha is filled within the root canal to seal a space within the root canal and shield an infectious route between the root canal and a periodontal tissue, or between the root canal and an oral cavity, thereby undergoing the root canal treatment.

Now, in order to achieve the root canal treatment, first of all, a dental pulp is removed, and root canal formation is then performed to enlarged a root canal, using an instrument such as a reamer and a file. Subsequently, the root canal is subjected to chemical cleaning by applying a chemical within the root canal after the enlargement. However, the root canal is complicated, and the number of root canals per tooth is different depending on a site at which the teeth are present. Namely, for example, a single root canal, two root canals, three root canals, or four root canals are present. Further, the shape of the root canal varies depending on the individual teeth, including a linear shape, a flat shape, and a curved shape. For these reasons, there may be a possibility that even when such a treatment is achieved, bacteria within the root canal cannot be removed completely, and therefore, even when the remedy is made to proceed, a toothache or a swelling of gingiva takes place by the infection of the remaining bacteria. In such case, it is necessary to carry out again the root canal treatment.

Thus, as a treatment for preventing this possibility from occurrence, root canal disinfection is taken. As this operation, employed is a process in which a calcium hydroxide-based root canal filler containing calcium hydroxide is filled temporarily within the root canal, thereby effecting disinfection utilizing a strong alkalinity of the calcium hydroxide. And, the following process is usually carried out. That is, after this treatment as the root canal disinfection has been completed, the root canal is washed with water, the moisture is removed, and a final root canal filler such as gutta-percha is then filled within the root canal.

The calcium hydroxide-based root canal filler has the following characteristics. That is, it not only has a soft effect rather than the strong transient sterilization effect, but also promotes the formation of a hard tissue by the matter that the calcium hydroxide is converted into calcium carbonate by carbon dioxide coming from a living body or the like, which is then fixed within the root canal, so that one can expect biological sealing of an apical foramen, and it is gentle to living bodies. These characteristics are ones never seen in other preparations. In the case where infectious diseases such as apical periodontitis unfortunately occur during the treatment of root canal disinfection with the calcium hydroxide-based root canal filler, it is necessary to surely remove the carbonated calcium hydroxide-based root canal filler reaching the root apex, eliminate the infected portion, and do the treatment with the chemical again. However, what the calcium hydroxide-based root canal filler having been gradually converted into calcium carbonate and fixed within the root canal is eliminated from the root canal having a complicated shape as described above by a mechanical cutting method with, for example, a reamer and a file, is a very difficult method and takes a long period of time. Also, there may be a possibility that infectious diseases such as inflammations again occur from a part of the infected portion that has not been eliminated within the root canal. Further, there may be a possibility that during cutting out by mechanical cutting with, for example, a reamer and a file, the root canal is cut out unnecessarily. Moreover, in many cases, the infection occurred during the root canal disinfection is caused by bacteria having been unable to be sterilized only by calcium hydroxide, or the like. In these cases, after removing the carbonated calcium hydroxide-based root canal filler, it is necessary to carry out another disinfection with, for example, an iodine preparation.

SUMMARY OF THE INVENTION

Under such background, the invention is aimed to provide a solubilizing agent of a carbonated calcium hydroxide-based root canal filler, by which during doing the root canal treatment again, the calcium hydroxide-based root canal filler that has been carbonated and fixed within a root canal can be surely eliminated from the root canal within a short period of time, and at the same time, the inside of the root canal can be sterilized.

In order to achieve the above-described aim, we, the present inventors made extensive and intensive investigations. As a result, it has been found that in order to remove a calcium hydroxide-based root canal filler, which after the root canal filling, has been gradually converted into calcium carbonate by carbon dioxide coming from a living body or the like and fixed on a root canal wall, when a solubilizing agent of a carbonated calcium hydroxide-based root canal filler, comprising water having a specific acid and a specific sterilizing properties-imparting agent compounded therewith, is used, the calcium carbonate can be readily dissolved within a short period of time, and at the same time, the inside of the root canal can be sterilized, leading to the accomplishment of the present invention.

Specifically, the solubilizing agent of the carbonated calcium hydroxide-based root canal filler according to the present invention comprises water containing at least one acid selected from the group consisting of phosphoric acid, gluconic acid, fumaric acid, lactic acid, glycolic acid, propionic acid, malic acid, maleic acid, citric acid, succinic acid, tartaric acid, acetic acid, glycerophosphoric acid, and malonic acid; and at least one sterilizing properties-imparting agent selected from the group consisting of an iodine preparation, a surfactant, a bactericide, hydrogen peroxide, and limonene. It is preferred that the amount of the at least one selected from the group consisting of phosphoric acid, gluconic acid, fumaric acid, lactic acid, glycolic acid, propionic acid, malic acid, maleic acid, citric acid, succinic acid, tartaric acid, acetic acid, glycerophosphoric acid, and malonic acid is 1 to 60% by weight of the whole; and that the amount of the at least one sterilizing properties-imparting agent selected from the group consisting of an iodine preparation, a surfactant, a bactericide, hydrogen peroxide, and limonene is 0.1 to 30% by weight of the whole.

DETAILED DESCRIPTION OF THE INVENTION

In the solubilizing agent of the carbonated calcium hydroxide-based root canal filler according to the present invention, the acid is used to dissolve the calcium hydroxide-based root canal filler that has been carbonated and fixed within the root canal and remove it. Since this acid is required to be safe against living bodies during the use within an oral cavity, the kind of the acid that can be used is, as a matter of course, limited. That is, from the viewpoint of the solubilizing agent of the carbonated calcium hydroxide-based root canal filler, a decalcification action against teeth should not be strong and an ability for reacting with calcium carbonate and dissolving it therein is required. The acid that can be used for the solubilizing agent of the carbonated calcium hydroxide-based root canal filler according to the present invention is at least one selected from the group consisting of phosphoric acid, gluconic acid, fumaric acid, lactic acid, glycolic acid, propionic acid, malic acid, maleic acid, citric acid, succinic acid, tartaric acid, acetic acid, glycerophosphoric acid, and malonic acid. Needless to say, the acid is limited to those not only having a solubility of the fixed calcium hydroxide-based root canal filler but also being harmless to living bodies. It is preferred that an amount of the at least one selected from the group consisting of phosphoric acid, gluconic acid, fumaric acid, lactic acid, glycolic acid, propionic acid, malic acid, maleic acid, citric acid, succinic acid, tartaric acid, acetic acid, glycerophosphoric acid, and malonic acid, which is contained in the solubilizing agent of the carbonated calcium hydroxide-based root canal filler according to the present invention, is 1 to 60% by weight in the solubilizing agent for the calcium hydroxide-based root canal filler. When the amount of the acid is less than 1% by weight, the solubilizing effect of the carbonated calcium hydroxide-based root canal filler is hardly obtained; and on the other hand, when the acid is compounded in an amount exceeding 60% by weight, the decalcification action against teeth is so strong that a possibility of damaging a tooth tends to increase.

The sterilizing properties-imparting agent that is used for the solubilizing agent of the carbonated calcium hydroxide-based root canal filler according to the present invention is used for sterilizing bacteria that have not been sterilized by the calcium hydroxide-based root canal filler, simultaneously with the dissolution and removal of the calcium hydroxide-based root canal filler. Examples of the sterilizing properties-imparting agent that can be used in the present invention include an iodine preparation, a surfactant, a bactericide, hydrogen peroxide, and limonene. It is preferred that the at least one sterilizing properties-imparting agent selected from the group consisting of an iodine preparation, a surfactant, a bactericide, hydrogen peroxide, and limonene is compounded in an amount of 0.1 to 30% by weight in the solubilizing agent of the carbonated calcium hydroxide-based root canal filler. When the amount of the sterilizing properties-imparting agent is less than 0.1% by weight, the sterilization effect is hardly obtained; and on the other hand, when the sterilizing properties-imparting agent is compounded in an amount exceeding 30% by weight, the biodetrimental action is possibly strong.

Examples of the iodine preparation include povidone iodine and iodine-containing potassium iodide. The povidone iodine is a composite of iodine and polyvinylpyrrolidone. The iodine in such iodine preparations inhibits a cell function due to its oxidation action to exhibit a strong sterilization action against bacteria. These iodine preparations are also useful against mycetes and viruses.

The surfactant to be used for the solubilizing agent of the carbonated calcium hydroxide-based root canal filler according to the present invention is a substance that generally reduces a surface tension. At the same time, the surfactant has a strong sterilization action over a wide range, as represented by benzethonium chloride or the like. As the surfactant, preferred are anionic surfactants, and examples include aliphatic quaternary ammonium salts, pyridinium salts and imidazolium salts, in addition to benzethonium chloride and benzalkonium chloride.

The bactericide is a substance having a bactericidal action, an antiviral action, enzyme inhibitory action, and an immunomodification action, which are produced mainly by microorganisms, and its efficacy spreads to Gram-positive bacteria, Gram-negative bacteria, acidophil bacteria, ray fungi, molds, viruses, and the like. As the bactericide, useful are not only chemical substances such as chlorhexidine but also generally used antibiotics. Examples of the antibiotics include penicillin-based antibiotics such as penicillin G potassium, Pentrex, Methocillin S, Pentcillin, and Unasyn S; Cepham-based antibiotics such as Cefamedin, Cefmetazone, Takesulin, Cefotax, and Modacin; aminoglycoside-based antibiotics such as Tobracin, Gentacin, Amikamycin, Kanamycin, Streptomycin, and Fradiomycin; macrolide-based antibiotics such as Leucomycin and Dalacin S; and tetracycline-based antibiotics such as Minomycin. Also, can be enumerated other antibiotics such as chloramphenicol-based antibiotics, peptide-based antibiotics, griseofulvin-based antibiotics, and polyene-based antibiotics.

The hydrogen peroxide that is used for the solubilizing agent of the carbonated calcium hydroxide-based root canal filler according to the present invention is one used widely as a sterilizing properties-imparting agent in the dentistry. Particularly, in the present invention, when it is used in combination with acetic acid, a higher sterilization effect can be expected. Further, the limonene that is used for the solubilizing agent of the carbonated calcium hydroxide-based root canal filler according to the present invention is one kind of monocyclic monoterpenes, and any of d-limonene and l-limonene can be used.

The solubilizing agent of the carbonated calcium hydroxide-based root canal filler according to the present invention is used in the following method. That is, first of all, the calcium hydroxide-based root canal filler that has been filled within the root canal, carbonated and fixed within the root canal, or the calcium hydroxide-based root canal filler used as a sealer for root canal filling, is eliminated using a reamer and a file by the usual root canal enlargement operation. Thereafter, the solubilizing agent of the carbonated calcium hydroxide-based root canal filler according to the present invention is poured into the root canal, and after standing for a while, the solubilizing agent of the carbonated calcium hydroxide-based root canal filler is eliminated from the root canal upon washing with water. At this time, instead of standing, when the solubilizing agent of the carbonated calcium hydroxide-based root canal filler is stirred using a blade-less instrument such as a lentula and a broach, an improvement of the solubilizing effect can be expected.

As a matter of course, to the solubilizing agent of the carbonated calcium hydroxide-based root canal filler according to the present invention, may be added colorants and the like so far as the characteristics are not hindered.

Now, the invention will be described in detail with reference to the following Examples, but it should not be construed that the invention is limited thereto.

EXAMPLE 1

Water (62% by weight) was mixed with 13% by weight of citric acid and 25% by weight of d-limonene (a trade name:

Orange Cleaner 18, made by Yasuhara Chemical Co., Ltd.) to prepare a solubilizing agent of a carbonated calcium hydroxide-based root canal filler. The solubilizing agent of the carbonated calcium hydroxide-based root canal filler was subjected to the following tests: "Solubility of carbonated calcium hydroxide-based root canal filler", "Observation within root canal after removal of carbonated calcium hydroxide-based root canal filler", and "Sterilizing properties of solubilizing agent of carbonated calcium hydroxide-based root canal filler".

(Solubility of Carbonated Calcium Hydroxide-based Root Canal Filler)

A calcium carbonate column formed in a size having a diameter of 1 mm and a length of 15 mm was immersed in 25 ml of the solubilizing agent of the carbonated calcium hydroxide-based root canal filler. After standing at 23° C. for 10 minutes, the state of the calcium carbonate column was visually observed and evaluated according to the following criteria.

A: The calcium carbonate column is dissolved and falls.
B: The surface of the calcium carbonate column is dissolved and breaks or becomes thin.
C: The change of the calcium carbonate column is not substantially observed.

(Observation Within Root Canal After Removal of Carbonated Calcium Hydroxide-based Root Canal Filler)

A standard human maxillary incisor tooth, which had been preserved in a 10% formalin solution after tooth extraction, was used as a sample. The human maxillary incisor tooth was cut in a tip thereof and subjected to pulp chamber spreading, followed by subjecting to usual root canal enlargement operation to form a root canal. A commercially available calcium hydroxide powder (60% by weight) was uniformly mixed with 40% by weight of distilled water having been colored blue for discrimination from a root canal wall, by means of a spatula to prepare an even slurry, which was then filled within the root canal by means of a lentula. The resulting sample was allowed to stand in an atmosphere at a constant temperature of 37° C. and at a humidity of 100% and having a $CO_2$ concentration of 5% for 7 days. Thereafter, the carbonated calcium hydroxide-based root canal filler was carefully removed using a reamer and a file, while paying attention such that the root canal was not enlarged. Then, the solubilizing agent of the carbonated calcium hydroxide-based root canal filler was poured into the root canal, and the carbonated calcium hydroxide-based root canal filler remaining within the root canal was dissolved and removed using a file, followed by washing with water. The sample was cut, and the inside of the root canal was visually observed. Thus, the state within the root canal after removal of the carbonated calcium hydroxide-based root canal filler was evaluated according to the following criteria of three grades A to C.

Further, an example, in which the carbonated calcium hydroxide-based root canal filler was removed only through the removal using a reamer and a file, was designated as Comparative Example 1.

A: The carbonated calcium hydroxide-based root canal filler is removed from the root canal wall.
B: The carbonated calcium hydroxide-based root canal filler remains a little on the root canal wall.
C: The carbonated calcium hydroxide-based root canal filler remains on the root canal wall.

(Sterilizing Properties of Solubilizing Agent of Carbonated Calcium Hydroxide-based Root Canal Filler)

Using *Escherichia coli* as a bacterium kind, the number of live bacteria after cultivation for 24 hours was counted and evaluated according to the following criteria, as compared with Comparative Example 2 containing no sterilizing properties-imparting agent.

A: 1/10 or less of Comparative Example 2
B: 1/3 or less of Comparative Example 2
C: Equivalent number of Comparative Example 2

With respect to Examples 2 to 16 and Comparative Example 2, the respective tests were carried out in the same manner as in Example 1. The compounding amounts of the components (with the remainder being water) and the test results are summarized and shown in Table 1.

TABLE 1

| | Acid | Sterilizing properties-imparting agent | Solubility of carbonated calcium hydroxide-based root canal filler | Observation within root canal after removal of carbonated calcium hydroxide-based root canal filler | Sterilizing properties of solubilizing agent of carbonated calcium hydroxide-based root canal filler |
|---|---|---|---|---|---|
| Example 1 | Citric acid (13% by weight) | d-Limonene (25% by weight) | A | A | A |
| Example 2 | Acetic acid (2% by weight) | Povidone iodine (3% by weight) | A | B | A |
| Example 3 | Gluconic acid (17% by weight) | Benzethonium chloride (2% by weight) | B | B | A |
| Example 4 | Maleic acid (10% by weight) | Povidone iodine (1% by weight) | A | B | A |
| Example 5 | Citric acid (15% by weight) | Benzalkonium chloride (1% by weight) | A | A | A |
| Example 6 | Acetic acid (3% by weight) | d-Limonene (15% by weight) | A | A | A |
| Example 7 | Phosphoric acid (3% by weight) | Povidone iodine (2% by weight) | A | B | A |
| Example 8 | Lactic acid (2% by weight) | Cefamedin (1% by weight) | A | B | A |

TABLE 1-continued

|  | Acid | Sterilizing properties-imparting agent | Solubility of carbonated calcium hydroxide-based root canal filler | Observation within root canal after removal of carbonated calcium hydroxide-based root canal filler | Sterilizing properties of solubilizing agent of carbonated calcium hydroxide-based root canal filler |
|---|---|---|---|---|---|
| Example 9 | Phosphoric acid (5% by weight) | Potassium iodide containing 0.5% by weight of iodine (10% by weight) | A | B | A |
| Example 10 | Phosphoric acid (10% by weight) | Chlorhexidine gluconic acid (1% by weight) | A | A | A |
| Example 11 | Acetic acid (5% by weight) | Hydrogen peroxide (2% by weight) | A | A | A |
| Example 12 | Propionic acid (13% by weight) | Benzethonium chloride (15% by weight) | A | B | A |
| Example 13 | Phosphoric acid (0.5% by weight) Acetic acid (2% by weight) | Hydrogen peroxide (2% by weight) | A | A | A |
| Example 14 | Malonic acid (25% by weight) | Chlorhexidine gluconic acid (1% by weight) | A | A | A |
| Example 15 | Phosphoric acid (55% by weight) | Potassium iodide containing 1% by weight of iodine (10% by weight) | A | A | A |
| Example 16 | Citric acid (50% by weight) | Potassium iodide containing 0.5% by weight of iodine (10% by weight) | A | A | A |
| Comparative Example 1 | — | — | — | C | — |
| Comparative Example 2 | Ascorbic acid (25% by weight) | — | B | B | — |

As is evident from the Examples and Comparative Examples as shown in Table 1, it has been confirmed that as compared with the case of the conventional mechanical cutting and removal of the carbonated calcium hydroxide-based root canal filler only by means of a reamer and a file (Comparative Example 1), not only the solubilizing agent of the carbonated calcium hydroxide-based root canal filler according to the present invention can surely remove the calcium hydroxide-based root canal filler, but also a good sterilization effect brought by the sterilizing properties-imparting agent can be obtained.

As described above, the solubilizing agent of the carbonated calcium hydroxide-based root canal filler according to the present invention can not only more surely remove the carbonated calcium hydroxide-based root canal filler, that remains within a root canal, even after a carbonated calcium hydroxide-based root canal filler has been tried to be removed using a reamer and a file from a root canal during the conventional re-remedy of the root canal by a simple operation, but also sterilize bacteria which the calcium hydroxide-based root canal filler cannot sterilize. Accordingly, the solubilizing agent of the carbonated calcium hydroxide-based root canal filler according to the present invention is very valuable in contributing to the dental remedy.

While the invention has been described in detail and with reference to specific embodiments thereof, it will be apparent to one skilled in the art that various changes and modifications can be made therein without departing from the spirit and scope thereof.

What is claimed is:

1. A method for solubilizing a carbonated calcium hydroxide-based root canal filler, comprising solubilizing the filler with a solubilizing agent which comprises water containing at least one acid selected from the group consisting of phosphoric acid, gluconic acid, fumaric acid, lactic acid, glycolic acid, propionic acid, malic acid, maleic acid, citric acid, succinic acid, tartaric acid, acetic acid, glycerophosphoric acid, and malonic acid; and at least one sterilizing properties-imparting agent selected from the group consisting of an iodine preparation, a surfactant, a bactericide, hydrogen peroxide, and limonene.

2. The method as claimed in claim 1, wherein said at least one acid is compounded in an amount of 1 to 60% by weight of the solubilizing agent; and said at least one sterilizing properties-imparting agent is compounded in an amount of 0.1 to 30% by weight of the solubilizing agent.

* * * * *